United States Patent [19]

Oeda et al.

[11] 4,291,018

[45] Sep. 22, 1981

[54] LIPSTICK OF THE CORE-SHEATH TYPE

[75] Inventors: Ichiro Oeda; Isao Sano, both of Odawara, Japan

[73] Assignee: Kanebo Ltd., Tokyo, Japan

[21] Appl. No.: 13,372

[22] Filed: Feb. 21, 1979

[30] Foreign Application Priority Data

Feb. 23, 1978 [JP] Japan .................................. 53-20150

[51] Int. Cl.³ ...................... A61K 7/025; A61K 7/027
[52] U.S. Cl. ................................ 424/64; 424/DIG. 5
[58] Field of Search ........................ 424/64, DIG. 5

[56] References Cited

U.S. PATENT DOCUMENTS

| | | | |
|---|---|---|---|
| 1,320,855 | 11/1919 | Henderson | 424/DIG. 5 |
| 1,576,567 | 3/1926 | Bonanno | 424/DIG. 5 |
| 2,523,683 | 9/1950 | Mario | 424/DIG. 5 |
| 2,566,722 | 9/1951 | Friedberg | 424/DIG. 5 |
| 2,626,847 | 1/1953 | Brown | 424/DIG. 5 |
| 2,628,624 | 2/1953 | Mario | 424/DIG. 5 |
| 2,853,422 | 9/1958 | Jarrett | 424/64 |
| 2,873,229 | 2/1959 | Wick | 424/64 |
| 3,201,314 | 8/1965 | Morshauser et al. | 424/64 |
| 3,211,619 | 10/1965 | Buckwalter et al. | 424/DIG. 5 |
| 3,279,999 | 10/1966 | Harrison et al. | 424/64 X |
| 3,947,571 | 3/1976 | Murphy et al. | 424/64 |

FOREIGN PATENT DOCUMENTS

| | | | |
|---|---|---|---|
| 647759 | 11/1964 | Belgium | 424/64 |
| 752558 | 12/1970 | Belgium | 424/64 |
| 2335549 | 2/1975 | Fed. Rep. of Germany | 424/64 |
| 2358139 | 2/1978 | France | 424/64 |
| 424845 | 9/1947 | Italy | 424/64 |
| 46-32679 | 9/1971 | Japan | 424/64 |
| 50-13542 | 2/1975 | Japan | 424/64 |
| 519913 | 4/1972 | Switzerland | 424/64 |
| 1205114 | 9/1970 | United Kingdom | 424/64 |
| 1206542 | 9/1970 | United Kingdom | 424/64 |

*Primary Examiner*—Dale R. Ore

[57] ABSTRACT

This invention relates to a lipstick having a construction of the core-sheath type which comprises two different compositions A and B arranged in core-sheath relationship, the composition A consisting essentially of a homogeneous mixture of from 53 to 85% by weight of a low-viscosity oily ingredient having a viscosity of less than approximately 80 centipoises at 36° C. and from 15 to 47% by weight of a waxy ingredient having the form of a solid at 36° C. and the composition B consisting essentially of a homogeneous mixture of from 40 to 90% by weight of a viscous oily ingredient having a viscosity of at least 200 centipoises at 36° C. and from 10 to 60% by weight of said waxy ingredient. When applied to the lips, this lipstick causes no tacky or disagreeable sensation, spreads well with a soft feel and a light touch, adheres evenly to the lips and gives protection thereto, and provides a good and beautiful gloss, clarity, hue, and color development.

9 Claims, 5 Drawing Figures

LIPSTICK OF THE CORE-SHEATH TYPE

BACKGROUND OF THE INVENTION:

(1) Field of the Invention:

This invention relates to lipsticks having a construction of the core-sheath type (hereinafter referred to as "lipsticks of the core-sheath type") which comprises two different compositions arranged in core-sheath relationship along the longitudinal axis thereof and, more particularly, to an excellent lipstick of the core-sheath type which, when applied to the lips by contact with its smooth end surface intersecting the longitudinal axis thereof and having the core exposed therein, causes no tacky or disagreeable sensation, spreads well with a soft feel and a light touch, adheres evenly to the lips and gives protection thereto, and provides a good and beautiful gloss, clarity, hue, and color development.

(2) Description of the Prior Art:

The quality characteristics of conventional lipstick have the nature of a trade-off in which some characteristics cannot be improved without sacrificing others. It is difficult, therefore, to produce those lipsticks which have all of desirable properties, such as beautiful gloss, high clarity, soft feel, good adhesion, lack of tackiness and slipperiness, good color development, and moderate strength.

(1) For example, if those materials, such as low-viscosity oily ingredients, which can provide a light touch, soft feel, good spreadability, and high clarity are used in large amounts, the resulting lipstick is liable to stain the tableware and the clothes, apt to run out of the lips and impair the makeup, and easy to break.

(2) If those materials, such as viscous oily ingredients, which serve to overcome the disadvantages described in (1) are used in large amounts, the resulting lipstick fails to spread well and causes tacky and disagreeable sensations to the lips.

(3) Any attempt to overcome the disadvantages described in (2) leads to recurrence of the disadvantages described in (1).

(4) If both of the above-described materials are used in large amounts for the purposes of overcoming all the disadvantages described in (1) and (2), their effects offset each other. Thus, it is impossible to obtain any lipstick exhibiting all of the avove-described desirable properties.

Meanwhile, a number of composite lipsticks have been proposed. They include, for example, a lipstick of the side-by-side type in which two different compositions are bonded along the longitudinal axis thereof and a lipstick of the core-sheath type in which a core consisting of one composition is surrounded by a sheath consisting of another composition or wax. However, these composite lipsticks have many shortcomings and are of little utility for practical purposes.

Specifically, in the lipsticks of the side-by-side type disclosed in Japanese Utility Model Publications No. 17599/'62 and No. 17600/'62', two masses of compositions having different colors and densities are bonded in a vertical plane. These lipsticks can produce a wide variety of color-coordinated cosmetic effects adapted for the season and opportunity, which effects are usually achievable only with two or more simple lipsticks having different colors and densities. However, they have the disadvantage of tending to undergo a separation of both compositions because they must be applied by holding them in a slightly tilted position and pressing them on the lips.

In the bordering lipstick described in Japanese Utility Model Laying-open Publication No. 135377/75', a thin core of lip rouge is surrounded by a layer of hard wax. This lipstick permits an elaborate makeup and has an hygienic advantage in that the core is not touched with the hand. However, the core is easy to break and the sheath (of hard wax) need be sharpened as the core wears away. Moreover, the sheath cannot be used as the core wears away. Moreover, the sheath cannot be used as lip rouge.

In the lipstick of the core-sheath type described in U.S. Pat. No. 3,279,999, the difference in hardness (or melting point) between the core and sheath compositions is unduly great and the content of low-viscosity oily ingredients (namely, peanut oil and butyl stearate) in the core or sheath composition is very low. As a result, the softer composition wears away so rapidly that the core becomes depressed or sticks out. This makes it difficult to apply both compositions equally to the lips. Moreover, this lipstick has the disadvantages of being tending to slip during application, causing tacky, resistant, and disagreeable sensations to the lips, and failing to provide a good gloss and a clear appearance.

In order to overcome all of the above-described disadvantages of conventional simple lipsticks and prior art composite lipsticks, the present inventors have performed intensive and extensive studies and found that an excellent lipstick of the core-sheath type can be obtained by using a composition A containing from 53 to 85% by weight of low-viscosity oily ingredient and another composition B consisting essentially of a viscous oily ingredient and a waxy ingredient. These compositions have both desirable properties and shortcomings, and are not suited to the formation of simple lipsticks or lipsticks of the side-by-side type. However, when they are formed into a lipstick of the core-sheath type, only the desirable properties of both compositions are enhanced and manifested owing to the unique synergistic effect of this invention, whereby satisfactory cosmetic effects are easily and readily produced on the lips.

SUMMARY OF THE INVENTION

It is the primary object of this invention to provide an excellent lipstick of the core-sheath type (such as lip rouge or lip cream preparation) which, when applied to the lips by contact with its end surface having the core exposed therein, shows no slipperiness, causes no tacky, resistant, or disagreeable sensation, spreads well with a soft feel and a light touch, adheres evenly to the lips and gives protection thereto, and provides a good and beautiful gloss, clarity, hue, and color development.

The foregoing and other objects of this invention are accomplished by providing a lipstick of the core-sheath type comprising two different compositions A and B arranged in coresheath relationship along the longitudinal axis thereof, said composition A consisting essentially of a homogeneous mixture of from 53 to 85% by weight of a low-viscosity oily ingredient having a viscosity of less than approximately 80 centipoises at 36° C. and from 15 to 47% by weight of a waxy ingredient having the form of a solid at 36° C. and said composition B consisting essentially of a homogeneous mixture of from 40 to 90% by weight of a viscous oily ingredient having a viscosity of at least approximately 200 centipoises at 36° C. and from 10 to 60% by weight of said waxy ingredient.

DETAILED DESCRIPTION OF THE PREFERRED EMBODIMENTS

Figure 1:
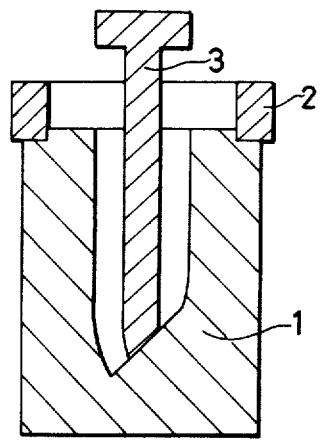
FIGS. 1 to 3 are vertical sectional views illustrating a procedure for molding a lipstick of the core-sheath type in accordance with this invention.

In accordance with this invention, a lipstick has a construction of the so-called core-sheath type in which two different compositions A and B are arranged in core-sheath relationship along the longitudinal axis thereof.

The compositions A and B are used in conjunction with each other. This means that the sheath consists of the composition B when the core consists of the composition A and that the core consists of the composition B when the sheath consists of the compositon A. The expression "low-viscosity oily ingredient having a viscosity of less than approximately 80 centipoises at 36° C.", as used herein, denotes oily substances which have a viscosity of less than approximately 80 centipoises as measured with a rotational viscometer at a specimen temperature of 36°±0.5° C. The preferred low-viscosity oily ingredients are exemplified by, but not limited to, mineral oil (22 cps.), squalane (35 cps.), isopropyl palmitate (25 cps.), isopropyl myristate (25 cps.), cetyl lactate (22 cps.), butyl stearate (16 cps.), myristyl lactate (22 cps.), octyldodecyl ricinoleate (51 cps.), octyldodecyl myristate (37 cps.), octyldodecyl oleate (30 cps.), propylene glycol monolaurate (22.5 cps.), cetyl ricinoleate, (73 cps.), 2-ethyl-hexyl-succinate (25 cps.), cetyl isooctanoate (25 cps.), stearyl isooctanoate (19 cps.), glyceryl tri-2-ethyl-hexanate (37.5 cps.), hexadecyl alcohol (25 cps.), oleyl alcohol (37.5 cps.), octyldodecanol (37.5 cps.), oleic acid (38 cps.), olive oil (46 cps.), cocoa butter (54 cps.), and the like. These low-viscosity oily ingredients may be used either alone or in combination, and incorporated (or included) either in one composition (for the core or the sheath) or in both compositions (for the core and the sheath).

The expression "viscous oily ingredient having a viscosity of at least approximately 200 centipoises at 36° C.", as used herein, denotes oily substances which have a viscosity of at least approximately 200 centipoises as measured with a rotational viscometer at a specimen temperature of 36°±0.5° C. The preferred viscous oily ingredients are exemplified by, but not limited to, lanolin (48,000 cps.), castor oil (300 cps.), lanolin oil (916 cps.), polybutene having an average molecular weight of from 500 to 2,500 (33,000 cps.), petrolatum (102,000 cps.), lanolin alcohol (12,000 cps.), and the like. These viscous oily ingredients may by used either alone or in combination, and incorporated (or included) either in one compositon (for the core or the sheath) or in both compositions (for the core and the sheath).

The expression "waxy ingredient having the form of a solid at 36° C.", as used herein, denotes oily substances which have the form of a solid at 36°±0.5° C. and defy the measurement of their viscosity with a rotational viscometer. The preferred waxy ingredients are exemplified by, but not limited to, beeswax, candelilla wax, carnauba wax, microcrystalline wax, ceresin, paraffin wax, spermaceti, cetyl alcohol, stearyl alcohol, hydrogenated cottonseed oil, hydrogenated castor oil, hydrogenated palm oil, and the like. These waxy ingredients may be used either alone or in combination, and incorporated (or included) homogeneously in both compositions (for the core and the sheath).

The composition A comprises a homogeneous mixture of 53–85% by weight and preferably 55–75% by weight of the low-viscosity oily ingredient, 15–47% by weight and preferably 17–30% by weight of the above-defined waxy ingredient and 0–32% by weight and preferably 8–28% by weight of the viscous oily ingredient, based on the total weight of the mixture.

If the content of the low-viscosity oily ingredient is lower than 53% by weight, the resulting compositon causes tacky and severely disagreeable sensations and tends to show a reduction in spreadability and clarity. If it is higher than 85% by weight, the resulting composition is readily worn away when used for the core, or is difficult to form and easy to break when used for the sheath. However, the compositions containing from 53 to 85% by weight of a low-viscosity oily ingredient have a light touch and a soft feel and provide good spreadability, clarity, and the like. These desirable properties are equally imparted to all the lipsticks of the core-sheath type including lip rouge preparations and other lip cosmetics, such as lip cream, containing no colorant.

As noted above, the composition A contains the above-defined waxy ingredient in an amount of from 15 to 47% by weight and preferably from 17 to 30% by weight based on the total weight of the mixture. If the content of this ingredient is lower than 15% by weight, the resulting compositon is difficult to form into a stick and easy to break. If it is higher than 47% by weight, the resulting composition shows a reduction in spreadability and tends to cause disagreeable sensations.

The compositon A may contain the above-defined viscous oily ingredient in an amount of from 0 to 32% by weight and preferably from 8 to 28% by weight. If the content of this ingredient is higher than 32% by weight, the resulting composition undesirably causes a severely tacky sensation and becomes difficult to form into a stick.

The composition A need not necessarily contain the viscous oily ingredient. However, its adhesion to the lips and its effect of preventing impairment of the makeup can be improved by using this ingredient in an amount as described above. On the other hand, the composition B comprises a homogeneous mixture of 40–90% by weight and preferably 50–75% by weight of the above viscous oily ingredient, 10–60% by weight and preferably 15–30% by weight of the waxy ingredient and 0–30% by weight and preferably 5–20% by weight of the low-viscosity oily ingredient, based on the total weight of the mixture.

If the content of the viscous oily ingredient is lower than 40% by weight, the resulting composition is apt to "run" and hard to adhere to the lips. If it is higher than 90% by weight, the resulting compositon is difficult to form into a stick and liable to cause tacky and disagreeable sensations.

As noted above, the compositon B contains 10–60% by weight and preferably 15–30% by weight of the waxy ingredient by weight based on the tatal weight of the mixture. If the content of the waxy ingredient is lower than 10% by weight, the resulting composition is difficult to form into a stick and easy to break. If it is higher than 60% by weight, the resulting composition causes hard and disagreeable sensations and shows a reduction in spreadability and adhesion.

The compositon B may contain the above-defined low-viscosity oily ingredient in an amount of from 0 to 30% by weight based on the weight of the mixture. If the content of this ingredient is higher than 30% by weight, the resulting composition generally tands to "run" and shows a reduction in adhesion. Moreover, it is readily worn away when used for the core, or is difficult to form and easy to break when used for the sheath.

The compositon B need not necessarily contain the low-viscosity oily ingredient. However, a moderately soft feel, clear appearance, and good spreadability can be imparted thereto by using this ingredient in an amount as described above.

Usually, more disirable results can be obtained when the composition B contains the viscous oily ingredient in an amount of from 50 to 75% by weight, the waxy ingredient in an amount of from 15 to 30% by weight, and the low-viscosity oily ingredient in an amount of from 5 to 20% by weight, these amounts being based on the total weight of the homogeneous mixture.

In the lipsticks of the core-sheath type comprising the above-defined compositions A and B in accordance with this invention, most disirable results can be obtained when both compositons contain all of the low-viscosity oily ingredient, viscous oily ingredient, and waxy ingredient. Moreover, for the manifestation of desirable cosmetic effects of these lipsticks, it is particularly important that the ingredients for each composition are mixed homogeneously.

In each of the compositions A and B, all the oily and waxy ingredients constitute from 77 to 100% by weight and preferably from 83.5 to 99.5% by weight of the respective composition.

The composition A or B, or both, may further contain a pigment in an amount of from 0 to 20% by weight and preferably from 0.5 to 15% by weight based on the weight of the respective composition. If the content of the pigment is higher than 20% by weight, the resulting composition tends to feel rough.

In the case of an uncolored lip cosmetic (lip cream), the compositon A or B, or both, usually contains no pigment. In the case of a colored lip rouge preparation, however, a good color development and a bright hue can be provided by using a pigment in an amount as described above.

The pigments which can be used in the practice of this invention are inorganic and organic pigments. The preferred inorganic pigments are exemplified by titanium dioxide, zinc oxide, talc, kaolin, iron oxides, bismuth oxychloride, mica coated with titanium dioxide, and the like. The preferred organic pigments, which may be the pigments permitted by law, are exemplified by D & C Red No. 7, D & C Red No. 9, D & C Red No. 19, D & C Red No. 21, D & C Red No. 30, D & C Orange No. 17, FD & C Red No. 3 Aluminum Lake, FD & C Yellow No. 5 Aluminum Lake, D & C Yellow No. 10 Aluminum Lake, FD & C Blue No. 1 Aluminum Lake, and the like.

The composition A or B, or both, may further contain a dye in an amount of from 0 to 5% by weight and preferably from 0 to 3% by weight based on the weight of the respective composition.

The preferred dyes, which may be the coal tar dyes permitted by law, are exemplified by oil-soluble dyes such as D & C Red No. 21, D & C Orange No. 5, and the like.

Preferably, the above-described compositions A and B have melting points of from 60° to 75° C., and the temperature difference therebetween is from 0° to 5° C. If the melting point is lower than 60° C., the composition is too soft to retain its original stick form, while if it is higher than 75° C., the composition is too hard for application. If the temperature difference therebetween is greater than 5° C., the difference in hardness is so great that the composition having a lower melting point wears away more repidly. This makes it difficult to apply both compositions equally to the lips, so that the desirable properties of both compositions may fail to be fully exhibited.

The compositions A and B are used in a weight ratio ranging from 1:4 to 4:1 and preferably from 1:2 to 2:1. If the weight ratio is outside this range, the desirable properties and shortcomings of the composition used in the larger amount are manifested to a greater degree, so that the desirable properties of both compositions may fail to be fully exhibited.

Whichever compositions are used for the core and the sheath, the resulting lipstick of the core-sheath type enables one to accomplish the above-described object of this invention. However, the lipsticks of the core-sheath type in which the sheath consists of the composition A containing from 53 to 85% by weight of a low-viscosity oily ingredient are the most preferable, because they cause a more agreeable sensation to the lips and present a clear and glossy appearance.

In the lipsticks of the core-sheath type in accordance with this invention, the cross-sectional shapes of the core and the sheath may be, for example, circular, elliptic, oval, triangular, square, pentagonal, hexagonal, or rhombic. However, a substantially concentric construction is preferred because of the ease of formation.

The lipsticks of the core-sheath type in accordance with this invention are characterized by the fact that the desirable properties of both compositions are exhibited when they are applied to the lips by contact with both the core and the sheath exposed in the its end surface. It is preferable, therefore, that these lipsticks are formed with a smooth end surface intersecting the longitudinal axis thereof. This smooth end surface may be either perpendicular or inclined to the longitudinal axis.

The lipsticks of the core-sheath type in accordance with this invention can be made by preparing the compositions A and B separately and then molding them in a manner as will be described later. Specifically, the oily and waxy ingredients for each composition are mixed in predetermined proportions and heated, for example, to a temperature of from 85° to 90° C. In the resulting molten mass are homogeneously mixed predetermined amounts of necessary additives such as pigment, dye, perfume, and preservative. Then, the molten masses of compositions A and B thus obtained are formed into a lipstick.

Figure 2:
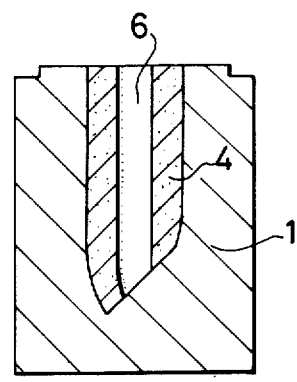
Figure 3:
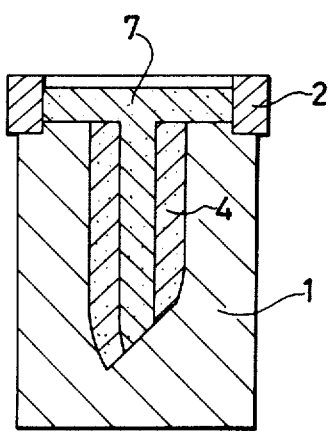

The formation of a lipstick of the core-sheath type in accordance with this invention can be carried out, for example, by the procedure illustrated in FIGS. 1 to 3. A mold is assembled which comprises a lower part 1 for molding the body of the lipstick and an upper part 2 for introducing the compositions thereinto. Into the cavity 4 (for example, of circular cross-section) so molded is inserted a rod 3 (for example, of circular cross-section) for forming a core (FIG. 1).

Then, a molten mass of the composition for the molding of the sheath is poured into the cavity 4 and cooled to solidify the composition. Thereafter, the rod 3 removed, the upper part 2 is demounted, and any superfluous composition is scraped off. Consequently, a core cavity 6 is molded as illustrated in FIG. 2.

After the upper part 2 is remounted, a molten mass 7 of the composition for the molding of the core is poured into the core cavity 6 and cooled to solidify the composition. (FIG. 3). Then, the upper part 2 is demounted and the molded product is removed from the lower part 1. Finally, this molded product is mounted in a suitable case to obtain a lipstick of the core-sheath type.

Lipsticks of the core-sheath type in which the core and the sheath have a variety of shapes as described above can be produced by changing the cross-sectional shapes of the cavity 4 and the rod 3 in the above-described mold.

The above-described composition A has a combination of desirable properties and shortcomings, while the above-described composition B has another combination of desirable properties and shortcomings. However, when a lipstick of the core-sheath type comprising these compositions A and B is applied to the lips, only the desirable properties of both compositions are enhanced and manifested owing to the unique synergistic effect of this invention. That is, when the lipstick is a lip cream preparation containing no colorant, it causes no tacky or disagreeable sensation to the lips, spreads well with a soft feel and a light touch, and adheres evenly and stably to the lips and gives protection thereto. When the lipstick is a lip rouge preparation containing a colorant or colorants in the core composition or in both compositons, it provides a good and beautiful gloss, clarity, hue, and color development in addition to the above-described effects. Thus, this lipstick is characterized by the ability to exhibit all of the properties desired for lipsticks.

It is evident from the results of the examples given below that these remarkable effects can be achieved solely by using the above-defined compositions A and B in a manner as described above and forming them into a lipstick of the core-sheath type.

This invention is further illustrated by the following examples. In these examples, all parts and percentages are by weight.

The appearance and properties of the lipsticks described therein were evaluated by organoleptic tests (Test of cosmetic action) using a panel composed of 50 women. The indicated values are the numbers of women who reported the presence of the corresponding properties. During the test period of 2 months, the lipsticks were daily applied to the lips in such a manner that both the core and the sheath thereof came into contact with the lips.

The viscosities (in cps.) of low-viscosity oily ingredients and viscous oily ingredients were measured with a Vismetron B rotational viscometer (manufactured by Tokyo Keiki Co., Japan). The No. 2 rotor was used for the oily ingredients having a viscosity of less than 1,000 cps. and the No. 4 rotor for those having a viscosity of 1,000 cps. or greater. The indicated values are the averages of 10 measurements.

The melting points of the core and sheath compositions were measured as follows: Each compositon was formed into a simple lipstick by conventional procedure and then subjected to measurement by Ubbelohde's method.

EXAMPLE 1

1. Formulations and Melting Points of Core and Sheath Compositions

TABLE 1

| Ingredient | Sheath Composition (parts) | Core Composition (parts) |
| --- | --- | --- |
| Candelilla Wax | 15.0 | 3.0 |
| Carnauba Wax | 2.0 | 2.0 |
| Ozokerite | 5.0 | 10.4 |
| Lanolin (48,000 cps.) | — | 15.0 |
| Castor Oil (300 cps.) | 16.8 | 49.7 |
| Octyldodecanol (37.5 cps.) | 25.0 | 10.0 |
| Cetyl Isooctanoate (25 cps.) | 35.0 | — |
| D & C Red No. 7 (pigment) | 0.2 | 2.0 |
| D & C Red No. 9 (pigment) | 0.3 | 3.0 |
| FD & C Red No. 3 Aluminum Lake (pigment) | — | 0.5 |
| Iron Oxides (pigment) | — | 0.5 |
| Titanium Dioxide (pigment) | — | 0.1 |
| D & C Red No. 21 (dye) | 0.1 | 0.2 |
| Antioxidant | 0.1 | 0.1 |
| Perfume | 0.5 | 0.5 |
| Total | 100 | 100 |
| Melting Point | 64° C. | 66° C. |
| Percentage by Weight | 66.6% | 33.3% |

2. Formation and Evaluation of Lipstick of Core-sheath Type

Figure 4:
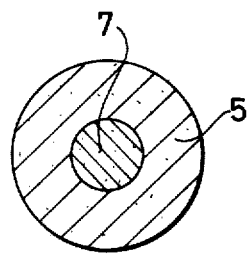
FIG. 4 is a cross-sectional view illustrating the construction of a lipstick of the core-sheath type formed in accordance with this invention.
Figure 5:
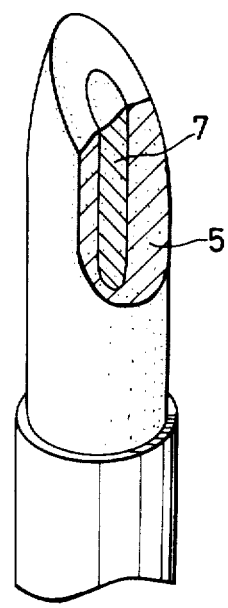
FIG. 5 is a partially cutaway perspective view of the lipstick of FIG. 4.

Each composition was prepared by mixing the above-described oily and waxy ingredients, heating them at 85°–90° C. to make a molten mass, and mixing the pigments, dye, perfume, and antioxidant therein The resulting molten mass of the sheath composition was poured into the cavity 4 of a mold as illustrated in FIG. 1 and cooled to solidify the composition. After removal of the rod 3, the core composition (in a molten state) was poured into the hollow body and cooled to form the core thereof. Thereafter, the cap 2 was demounted and the resulting lipstick of the core-sheath type having an inclined smooth end surface as illustrated in FIG. 5 was removed from the mold. As illustrated in the cross-sectional view of FIG. 4, this lipstick consisted of the core composition 7 and the sheath composition 5 in the weight ratio of 1:2 and had a concentric two-layer construction.

Then, an organoleptic test was performed on the abovedescribed lipstick of the invention, a comparative lipstick 1 (which was a simple lipstick consisting solely of the core composition), and a comparative lipstick 2 (which was a simple lipstick consisting solely of the sheath composition). The results are shown in Table 2.

TABLE 2

| Test Item | Lipstick of the Invention | Comparative Lipstick 1 | Comparative Lipstick 2 |
| --- | --- | --- | --- |
| Clear Appearance | 44 | 2 | 45 |
| Agreeable Touch | 43 | 15 | 48 |
| Good Adhesion | 37 | 41 | 10 |
| Beautiful Gloss | 34 | 45 | 20 |
| Good Durability | 39 | 42 | 15 |
| Lack of Tackiness | 42 | 3 | 49 |
| Good Color Development | 48 | 49 | 1 |

As can be seen from these data, the lipstick of the invention had all of the properties desired for lipsticks, such as clear appearance, agreeable touch, good adhesion, beautiful gloss, good durability, and good color development. Thus, the lipstick of the invention combined and enhanced the desirable properties of the comparative lipsticks 1 and 2, thereby compensating for the shortcomings thereof. After the test period of 2 months, the core and the sheath were equally worn away with the inclined end surface remaining smooth, and kept in a strongly and stably bonded state.

EXAMPLE 2

The procedure of Example 1 was repeated except that the core composition was used for the sheath and the sheath composition for the core. A similar organoleptic test was performed on the resulting lipstick of the core-sheath type. As a result, "Agreeable Touch" was reported by 40 women, "Good Adhesion" by 38, "Beautiful Gloss" by 34, "Good Durability" by 40, "Lack of Tackiness" by 38, and "Good Color Development" by 45.

COMPARATIVE EXAMPLE 1

A mold having a semicylindrical cavity was covered with a flat plate. Then, a molten mass of the core composition described in Example 1 was poured into this cavity and cooled to solidify the composition. The flat plate was replaced by another mold having a similar semicylindrical cavity. Then, a molten mass of the sheath composition described in Example 1 was poured into this cavity and cooled to solidity the composition. Upon removal from the molds, a molded product was obtained which consisted of two different compositions in the weight ratio of 1:1, these composition forming two semicylindrical masses bonded together along the longitudinal axis. This is a composite lipstick of the side-by-side type as disclosed in Japanese Patent Publication No. 17099/'61, FIG. 2. Then, one end of the lipstick was properly shaped to form an inclined end surface as illustrated in FIG. 5.

A similar organoleptic test was performed on this lipstick of the side-by-side type. It was applied in such a manner that the interfacial region between both compositions came into contact with the lips. As a result, 36 women experienced a separation of both compositions after 10–15 days and 14 after 3–4 weeks. As for its quality, "Agreeable Touch" was reported by 28 women, "Good Adhesion" by 35, "Beautiful Gloss" by 29, "Good Durability" by 31, "Good Color Development" by 34, "Lack of Tackiness" by 15, and "Clear Appearance" by 10.

Thus, though the compositions falling within the scope of the invention were used, the composite lipstick of the side-by-side type tended to undergo a separation of both compositions after a short period of time owing to the pressure exerted during application. Moreover with respect to such characteristics as touch, adhesion, color development, durability, and gloss, this lipstick was inferior to the lipstick of the invention described in Example 1, indicating that the desirable properties of both compositions failed to be fully exhibited.

COMPARATIVE EXAMPLE 2

According to the Example described in U.S. Pat. No. 3,279,999, column 3, a softer composition (having a melting point of 75° C.) and a harder composition (having a melting point of 65° C.) were prepared. In these composition, D & C Red No. 7 was used as pigment and methylparaben as preservative.

The procedure of Example 1 was repeated except that the softer composition was used for the core and the harder composition for the sheath. A similar organoleptic test (Test of cosmetic action) was performed on the resulting lipstick of the coresheath type. As a result, "Clear Appearance" was reported by 2 women, "Agreeable Touch" by 18, "Good Adhesion" by 20, "Beautiful Gloss" by 11, "Good Durability" by 39, "Good Color Development" by 41, and "Lack of Tackiness" by 5.

The procedure of Example 1 was repeated once more, except that the softer composition was used for the sheath and the harder composition for the core. A similar organoleptic test was performed on the resulting lipstick of the core-sheath type. As a result, "Clear Appearance" was reported by 16 women, "Agreeable Touch" by 25, "Good Adhesion" by 26, "Beautiful Gloss" by 21, "Good Color Development" by 36, and "Lack of Tackiness" by 17.

Thus, these lipsticks were significantly inferior to the lipstick of the invention described in Example 1.

COMPARATIVE EXAMPLE 3

The procedure of Example 1 was repeated except that 20.0 parts of octyldodecanol, 28.0 parts of cetyl isooctanoate, and 28.0 parts of castor oil were used in the sheath composition. A similar organoleptic test was performed on the resulting lipstick of the core-sheath type. As a result, "Clear Appearance" was reported by 25 women, "Agreeable Touch" by 23, "Good Adhesion" by 31, "Beautiful Gloss" by 27, "Good Durability" by 47.

As can be seen from these data, the desirable properties of both compositions failed to be fully exhibited because the content of the low-viscosity oily ingredients in the composition A was Lower than 55% by weight based on the combined weight of the oily and waxy ingredients.

EXAMPLE 3

1. Formulations and Melting Points of Core and Sheath Compositions

TABLE 3

| Ingredient | Sheath Composition (parts) | Core Composition (parts) |
|---|---|---|
| Candelilla Wax | 12.5 | 5.0 |
| Ozokerite | 7.5 | 12.5 |
| Carnauba Wax | 2.0 | — |
| Microcrystalline Wax | — | 3.0 |
| Beeswax | — | 2.0 |
| Lanolin (48,000 cps.) | — | 5.0 |
| Castor Oil (300 cps.) | — | 57.7 |
| Isopropyl Myristate (25 cps.) | 15.0 | — |
| Octyldodecanol (37.5 cps.) | 15.0 | — |
| Cetyl Isooctanoate (25 cps.) | 24.24 | — |
| Olive Oil (46 cps.) | 18.2 | — |
| Butyl Stearate (16 cps.) | 5.0 | — |
| Oleyl Alcohol (37.5 cps.) | — | 10.0 |
| D & C Red No. 7 (pigment) | 0.01 | 1.0 |
| D & C Red No. 9 (pigment) | 0.2 | 2.0 |
| D & C Orange No. 17 (pigment) | 0.04 | 0.5 |
| Iron Oxides (pigment) | 0.01 | 0.5 |
| Antioxidant | 0.1 | 0.1 |
| Perfume | 0.7 | 0.7 |
| Total | 100 | 100 |
| Melting Point | 67° C. | 70° C. |

2. Formation and Evaluation of Lipstick of Core-Sheath Type the procedure of Example 1 was repeated except that the abovedescribed core and sheath compositions were used in the weight ratio of 1:1.

Then, a similar organoleptic test (Test of Cosmetic Action) was performed on the resulting lipstick of the invention, a comparative lipstick 3 (which was a simple lipstick consisting solely of the core composition), and a comparative lipstick 4 (which was a simple lipstick consisting solely of the sheath composition). The results are shown in Table 4.

TABLE 4

| Test Item | Lipstick of the Invention | Comparative Lipstick 3 | Comparative Lipstick 4 |
|---|---|---|---|
| Clear Appearence | 46 | 2 | 46 |
| Agreeable Touch | 42 | 16 | 45 |
| Good Adhesion | 36 | 39 | 9 |
| Beautiful Gloss | 33 | 43 | 21 |
| Good Durability | 39 | 41 | 14 |
| Lack of Tackiness | 43 | 2 | 48 |
| Good Color Development | 46 | 47 | 2 |

As can be seen from these data, the lipstick of the invention combined the desirable properties of the comparative lipsticks 3 and 4, thereby compensating for the shortcomings thereof. Moreover, the core and the sheath were equally worn away and kept in a strongly bonded state.

EXAMPLE 4

1. Formulations and Melting Points of Core and Sheath Compositions

TABLE 5

| Ingredient | Core Composition (parts) | Sheath Composition (parts) |
|---|---|---|
| Candelilla Wax | 15.0 | 8.0 |
| Carnauba Wax | 5.0 | 3.0 |
| Ozokerite | — | 5.0 |
| Beeswax | — | 4.0 |
| Castor Oil | 19.0 | 16.0 |
| Lanolin | — | 10.0 |
| Lanolin Oil (916 cps.) | — | 46.1 |
| Octyldodecanol | 15.0 | — |
| Mineral Oil (22 cps.) | 5.0 | — |
| Isopropyl Myristate | 15.0 | — |
| Cetyl Isooctanoate | 25.0 | — |
| Oleyl Alcohol (37.5 cps.) | — | 10.0 |
| D & C Red No. 7 (pigment) | 0.2 | 3.0 |
| D & C Red No. 8 (pigment) | 0.2 | — |
| D & C Red No. 30 (pigment) | — | 0.5 |
| D & C Red No. 21 (dye) | 0.2 | — |
| Antioxidant | 0.1 | 0.1 |
| Perfume | 0.3 | 0.3 |
| Total | 100 | 100 |
| Melting Point | 66° C. | 70° C. |

2. Formulation and Evaluation of Lipstick of Core-Sheath Type

The procedure of Example 1 was repeated except that the above-described core and sheath compositions were used. With respect to such characteristics as touch, adhesion, gloss, durability, color development, and lack of tackiness, the resulting lipstick of the core-sheath type was approximately as good as the lipstick of the invention described in Example 2. Specifically, the shortcomings of the sheath composition, such as tacky, resistant, and disagreeable sensations, and those of the core composition, such as poor adhesion, low durability, and slipperiness, were found to be compensated for.

EXAMPLE 5

1. Formulations and Melting Points of Core and Sheath Compositions

TABLE 6

| Ingredient | Sheath Composition (parts) | Core Composition (parts) |
|---|---|---|
| Candelilla Wax | 10.0 | 5.0 |
| Carnauba Wax | 3.0 | 2.0 |
| Ozokerite | 5.0 | 5.0 |
| Beeswax | 6.0 | 8.0 |
| Castor Oil | 9.5 | 43.25 |
| Lanolin | — | 12.0 |
| Lanolin Oil | — | 3.0 |
| Mineral Oil (22 cps.) | — | 5.0 |
| Octyldodecanol | 12.0 | 5.0 |
| Isopropyl Myristate | 35.0 | 5.0 |
| Butyl Stearate (16 cps.) | 4.0 | — |
| Myristyl Lactate (22 cps.) | 5.0 | — |
| Cetyl Ricinoleate (73 cps.) | 5.0 | — |
| D & C Orange No. 17 (pigment) | 3.0 | 2.0 |
| Iron Oxides (pigment) | 1.0 | 2.0 |
| Titanium Dioxide (pigment) | 1.0 | 2.0 |
| D & C Orange No. 5 (dye) | — | 0.2 |
| Antioxidant | 0.05 | 0.1 |
| Perfume | 0.45 | 0.45 |
| Total | 100 | 100 |
| Melting Point | 68° C. | 70° C. |

2. Formation and Evaluation of Lipstick of Core-Sheath Type

The procedure of Example 1 was repeated except that the abovedescribed core and sheath compositions were used in the weight ratio of 2:1. With respect to such characteristics as adhesion, durability, gloss, touch, color development, and lack of tackiness, the resulting lipstick of the core-sheath type was approximately as good as the lipstick of the invention described in Example 1.

EXAMPLE 6

1. Formulations and Melting Points of Core and Sheath Compositions

TABLE 7

| Ingredient | Sheath Composition (parts) | Core Composition (parts) |
|---|---|---|
| Candelilla Wax | 5.0 | — |
| Carnauba Wax | 3.0 | 5.0 |
| Paraffin Wax | 12.0 | 10.0 |
| Microcrystalline Wax | 5.0 | 3.0 |
| Beeswax | — | 3.0 |
| Lanolin | 2.5 | 10.0 |
| Castor Oil | 49.5 | 42.8 |
| Polybutene (33,000 cps.) | — | 7.5 |
| Oleyl Alcohol (37.5 cps.) | 30.0 | 5.0 |
| Isopropyl Myristate | 10.0 | — |
| Dioctyl Succinate (25 cps.) | 20.0 | — |
| Squalane (35 cps.) | — | 5.0 |
| D & C Red No. 7 (pigment) | 2.0 | 2.0 |
| D & C Red No. 9 (pigment) | 3.0 | 3.0 |
| Iron Oxides (pigment) | 1.5 | 1.5 |
| Titanium Dioxide (pigment) | 1.5 | 1.5 |
| Antioxidant | 0.05 | 0.2 |
| Perfume | 0.5 | 0.5 |
| Total | 100 | 100 |
| Melting Point | 66° C. | 69° C. |

2. Formation and Evaluation of Lipstick of Core-Sheath Type

The procedure of Example 1 was repeated except that the abovedescribed core and sheath compositions were used in the weight ratio of 1:2. With respect to such characteristics as adhesion, durability, gloss, touch, color development, and lack of tackiness, the resulting lipstick of the core-sheath type was approximately as good as the lipstick of the invention described in Example 1.

EXAMPLE 7

1. Formulations and Melting Points of Core and Sheath Compositions

TABLE 8

| Ingredient | Sheath Composition (parts) | Core composition (parts) |
|---|---|---|
| Candelilla Wax | 17.0 | 7.0 |
| Carnauba Wax | 6.0 | 3.0 |
| Ozokerite | — | 5.0 |
| Beeswax | — | 5.0 |
| Lanolin | — | 10.0 |
| Castor Oil | 16.9 | 59.7 |
| Isopropyl Myristate (25 cps.) | — | 10.0 |
| Oleyl Alcohol | 20.0 | — |
| Octyldodecyl Myristate (37 cps.) | 30.0 | — |
| Glyceryl Tri-2-ethyl-hexanate (37.5 cps.) | 10.0 | — |
| Antioxidant | 0.1 | 0.3 |
| Total | 100 | 100 |
| Melting Point | 64° C. | 68° C. |

2. Formation and Evaluation of Lipstick of Core-Sheath Type

The procedure of Example 1 was repeated except that the above-described core and sheath compositions were used in the weight ratio of 1:1. The resulting lipstick of the core-sheath type, in which the core consisted of uncolored lip rouge and the sheath consisted of lip cream, had a clear appearance and a beautiful gloss, caused no tacky or disagreeable sensation to the lips, spread well with a soft feel and a light touch, and adhered evenly and stably to the lips and gave protection thereto. Specifically, the shortcomings of the core composition, such as tacky, resistant, and disagreeable sensations, and those of the sheath composition, such as poor adhesion, low durability, and slipperiness, were found to be compensated for.

EXAMPLE 8

1. Formulations and Melting Points of Core and Sheath Compositions

TABLE 9

| Ingredient | Sheath Composition (parts) | Core Composition (parts) |
|---|---|---|
| Candelilla Wax | 15.0 | 5.0 |
| Carnauba Wax | 5.0 | .5.0 |
| Ozokerite | 5.0 | 10.0 |
| Beeswax | — | 5.0 |
| Lanolin | — | 15.0 |
| Castor Oil | 4.6 | 32.3 |
| Oleyl Alcohol | — | 10.0 |
| Isopropyl Myristate | — | 10.0 |
| Octyldodecanol | 10.0 | — |
| Octyldodecyl Myristate | 50.0 | — |
| Glyceryl Trioctanoate | 10.0 | — |
| D & C Red No. 7 (pigment) | — | 3.0 |
| D & C Red No. 9 (pigment) | — | 2.0 |
| Iron Oxides (pigment) | — | 1.0 |
| Titanium Dioxide (pigment) | — | 1.0 |
| D & C Red No. 21 (dye) | — | 0.2 |
| Antioxidant | 0.5 | 0.2 |
| Perfume | 0.1 | 0.3 |
| Total | 100 | 100 |
| Melting Point | 69° C. | 72° C. |

2. Formation and Evaluation of Lipstick of Core-Sheath Type

The procedure of Example 1 was repeated except that the above-described core and sheath compositions were used. The resulting lipstick of the core-sheath type, in which the core consisted of colored lip rouge and the sheath consisted of uncolored lip cream, had a clear appearance, caused no tacky or disagreeable sensation to the lips, spread well with a soft feel and a light touch, and adhered stably to the lips and provided a good and beautiful gloss, clarity, and color development thereto. Specifically, the shortcomings of the core composition, such as tacky, resistant, and disagreeable sensations, and those of the sheath composition, such as poor adhesion, low durability, and slipperiness, were found to be compensated for.

EXAMPLE 9

1. Formulations and Melting Points of Core and Sheath Compositions

TABLE 10

| Ingredient | Sheath Composition (parts) | Core Composition (parts) |
|---|---|---|
| Carnauba Wax | 7.0 | 3.0 |
| Ceresin | 5.0 | 12.0 |
| Beeswax | 2.5 | 5.0 |
| Candelilla Wax | 10.0 | — |
| Lanolin | — | 15.0 |
| Castor Oil | — | 57.0 |
| Oleyl Alcohol | 31.5 | 3.0 |
| Squalane | — | 5.0 |
| Mineral Oil | 15.0 | — |
| Cetyl Isooctanoate (25 cps.) | 25.0 | — |
| Butyl Stearate | 5.0 | — |
| Total | 100 | 100 |
| Melting Point | 66° C. | 70° C. |

2. Formation and Evaluation of Lipstick of Core-Sheath Type

The procedure of Example 1 was repeated except that the abovedescribed core and sheath compositions were used in the weight ratio of 1:1. The resulting lipstick of the core-sheath type, in which the core and the sheath consisted of two different types of uncolored lip cream, caused no tacky or disagreeable sensation to the lips, spread well with a soft feel and a light touch, and adhered evenly and stably to the lips and gave protection thereto. Specifically, the shortcomings of the sheath composition, such as slipperiness, poor adhesion, and low durabilty, and those of the core composition, such as tacky, resistant, and disagreeable sensation, were found to be compensated for.

EXAMPLE 10

1. Formulations and Melting Points of Core and Sheath Compositions

TABLE 11

| Ingredient | Sheath Composition (parts) | Core Composition (parts) |
|---|---|---|
| Candelilla Wax | 7.0 | 12.0 |
| Carnauba Wax | 3.0 | 3.0 |
| Ceresin | 13.0 | — |
| Beeswax | — | 5.0 |
| Castor Oil | — | 55.3 |
| Oleyl Alcohol | 10.0 | 15.0 |
| Glyceryl Trioctanoate | 51.9 | — |
| D & C Red No. 7 (pigment) | 4.0 | — |
| D & C Red No. 9 (pigment) | 2.0 | 5.0 |
| D & C Orange No. 17 (pigment) | 1.0 | 1.0 |
| Iron Oxides (pigment) | — | 2.0 |
| Titanium Dioxide (pigment) | — | 1.0 |

TABLE 11-continued

| Ingredient | Sheath Composition (parts) | Core Composition (parts) |
|---|---|---|
| D & C Red No. 21 (dye) | 0.5 | — |
| Antioxidant | 0.1 | 0.2 |
| Perfume | 0.5 | 0.5 |
| Total | 100 | 100 |
| Melting Point | 67° C. | 68° C. |

2. Formation and Evaluation of Lipstick of Core-Sheath Type

The procedure of Example 1 was repeated except that the above-described core and sheath compositions were used. The resulting lipstick of the core-sheath type caused no tacky sensation to the lips, spread well, and provided good color development, adhesion, and durability. Specifically the shortcomings of the core composition, such as tacky, resistant, and disagreeable sensations and heavy touch, and those of the sheath compositions, such as slipperiness and poor adhesion, were found to be compensated for.

What is claimed is:

1. In a lipstick of the core-sheath type comprising two different compositions A and B arranged in core-sheath relationship along the longitudinal axis thereof, the improvement wherein said composition A consists essentially of a homogeneous mixture of
   (i) from 55 to 75% by weight of a low-viscosity oily ingredient having a viscosity of less than approximately 80 centipoises at 36° C.;
   (ii) from 8 to 28% by weight of a viscous oily ingredient having a viscosity of at least approximately 200 centipoises at 36° C.; and
   (iii) from 17 to 30% by weight of a waxy ingredient which is solid at 36° C.;
   and wherein said composition B consists essentially of a homogeneous mixture of
   (iv) from 50 to 75% by weight of (ii);
   (v) from 15 to 30% by weight of (iii); and
   (vi) from 5 to 20% by weight of (i);
   said compositions A and B comprising from 77 to 100% by weight of the respective homogeneous mixture and having melting points of from 60° to 75° C. and the temperature difference therebetween being from 0° to 5° C.; the weight of the composition of the core with respect to that of the sheath being in a weight ratio ranging from 1:2 to 2:1.

2. The lipstick of claim 1 wherein said low-viscosity oily ingredient is a oily substance selected from the group consisting of mineral oil, squalane, isopropyl palmitate, isopropyl myristate, cetyl lactate, butyl stearate, myristyl lactate, octyldodecyl ricinoleate, octyldodecyl myristate, propylene glycol monolaurate, octyldodecyl oleate, cetyl ricinoleate, dioctyl succinate, cetyl isooctanoate, stearyl isooctanoate, glyceryl trioctanoate, hexadecyl alcohol, oleyl alcohol, octyldodecanol, oleic acid, olive oil, and cocoa butter.

3. The lipstick of claim 1 wherein said viscous oily ingredient is a oily substance selected from the group consisting of lanolin, castor oil, lanolin oil, polybutene having an average molecular weight of from 500 to 2,500, petrolatum, and lanolin alcohol.

4. The lipstick of claim 1 wherein said waxy ingredient is a oily substance selected from the group consisting of beeswax, candelilla wax, carnauba wax, microcrystalline wax, ceresin, paraffin wax, spermaceti, cetyl alcohol, stearyl alcohol, hydrogenated cottonseed oil, hydrogenated castor oil, and hydrogenated palm oil.

5. The lipstick of claim 1 wherein a of said compositions A and B, further contains a pigment in an amount of less than 20% by weight based on the weight of the composition.

6. The lipstick of claim 1 wherein one of said compositions A and B, further contains a dye in an amount of less than 3% by weight based on the weight of the composition.

7. The lipstick of claim 1 wherein a of said compositions A and B, further contains a pigment in an amount of from 0.5 to 15% by weight on the weight of the composition.

8. The lipstick of claim 7 wherein said pigment is a inorganic pigment selected from the group consisting of titanium dioxide, zinc oxide, talc, kaolin, iron oxides, bismuth oxychloride, and mica coated with titanium dioxide.

9. The lipstick of claim 7 wherein said pigment is a organic pigment selected from the group consisting of D & C Red No. 7, D & C Red No. 9, D & C Red No. 19, D & C Red No. 21, D & C Red No. 30, D & C Orange No. 17, FD & C Red No. 3 Aluminum Lake, FD & C Yellow No. 5 Aluminum Lake, D & C Yellow No. 10 Aluminum Lake, and FD & C Blue No. 1 Aluminum Lake.

* * * * *